United States Patent [19]

Suzuki et al.

[11] Patent Number: 5,010,084
[45] Date of Patent: Apr. 23, 1991

[54] IMIDAZOQUINOLONE DERIVATIVES

[75] Inventors: Fumio Suzuki, Mishima; Takeshi Kuroda; Yoshisuke Nakasato, both of Shizuoka; Kenji Ohmori, Mishima; Haruhiko Manabe, Shizuoka, all of Japan

[73] Assignee: Kyowa Hakko Kogyo Co., Ltd., Tokyo, Japan

[21] Appl. No.: 553,551

[22] Filed: Jul. 18, 1990

[30] Foreign Application Priority Data

Jul. 18, 1989 [JP] Japan .................................. 1-185087

[51] Int. Cl.⁵ .................... C07D 471/02; A61K 31/44
[52] U.S. Cl. ........................................ 514/293; 546/82
[58] Field of Search ............................ 514/293; 546/82

Primary Examiner—Mary C. Lee
Assistant Examiner—Joseph K. McKane
Attorney, Agent, or Firm—Fitzpatrick, Cella, Harper & Scinto

[57] ABSTRACT

Novel imidazoquinolone derivative represented by formula (I);

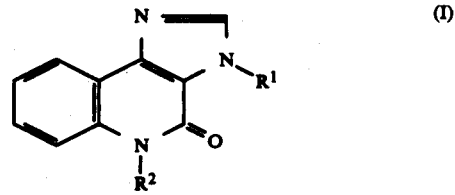

wherein $R^1$ represents lower alkyl or $-(CH_2)_m CO-R^3$ where $R^3$ represents hydrogen, lower alkyl, hydroxy or lower alkoxy; and m is an integer of 1 to 3; $R^2$ represents lower alkyl; or a pharmaceutically acceptable salt thereof.

4 Claims, No Drawings

IMIDAZOQUINOLONE DERIVATIVES

BACKGROUND OF THE INVENTION

The present invention relates to novel imidazoquinolone derivatives having 3H,5H-imidazo[4,5-c]quinolin-4-one skeleton and their pharmaceutically acceptable salts, which exhibit an antiallergic activity, bronchodilatory action and antiasthmatic activity.

1H-imidazo[4,5-c]quinolines useful as a bronchodilator and as an antiviral agent, represented by the following formula are disclosed in Japanese Published Unexamined Patent Application No. 123488/85 [U.S. Pat. Nos. 4698348 and 4689338, and EP-A-145340]

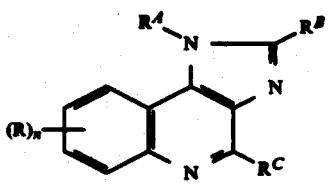

wherein $R^A$ represents hydrogen, alkyl, benzyl, phenyl, etc.; $R^B$ represents hydrogen, alkyl, etc.; and $R^C$ represents hydrogen, hydroxyl, alkylamino, etc.

In the commonly owned U.S. patent application Ser. No. 07/489,025 [Japanese Patent Application No. 54148/89], 1H,5H-imidazo[4,5-c]quinolin-4-one derivatives having a broncho-dilatory activity and an antiallergic activity are described.

SUMMARY OF THE INVENTION

An object of the present invention is to provide 3H,5H-imidazo[4,5-c]quinolin-4-one derivative show distinguished broncho-dilatory and/or antiallergic effect.

According to the present invention, there is provided an imidazoquinolone derivative represented by the formula (I);

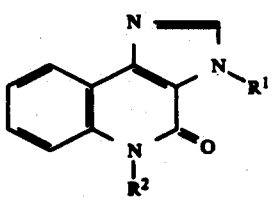

wherein $R^1$ represents lower alkyl or $-(CH_2)_m CO-R^3$ where $R^3$ represents hydrogen, lower alkyl, hydroxy or lower alkoxy; and m is an integer of 1 to 3; $R^2$ represents lower alkyl; or a pharmaceutically acceptable salt thereof.

DESCRIPTION OF THE INVENTION

In the definition of the respective groups in the formula (I), the lower alkyl or the alkyl moiety of the lower alkoxy means straight or branched alkyl having 1 to 6 carbon atoms and includes, for example, methyl, ethyl, n-propyl, isopropyl, n-butyl, isobutyl, sec-butyl, tert-butyl, n-pentyl, neopentyl, n-hexyl, etc.

The salts of Compound (I) include pharmaceutically acceptable acid addition salts, metal salts, ammonium salts, inorganic amine addition salts, amino acid addition salts, etc.

The pharmaceutically acceptable acid addition salts of Compound (I) include inorganic acid salts such as hydrochlorides, sulfates, phosphates, etc.; and organic acid salts such as acetates, maleates, fumarates, tartarates, citrates, etc. The pharmaceutically acceptable metal salts include alkali metal salts such as sodium salts, potassium salts, etc. and alkaline earth metal salts such as magnesium salts, calcium salts, etc.; aluminum salts, zinc salts, etc. The organic pharmaceutically acceptable amine addition salts include addition salts with morpholine, piperidine, etc. The pharmaceutically acceptable amino acid addition salts include addition salts of lysine, glycine, phenylalanine, etc.

Processes for preparing Compound (I) are set forth below.

When the defined groups are changed under the conditions of the following processes or are inadequate to proceeding of the following processes, processes can be readily carried out by a usual method in the organic synthetic chemistry, for example, by protection of functional groups, elimination of protecting groups.

Process 1

Compound (I) is obtained by reacting Compound (II) with Compound (III).

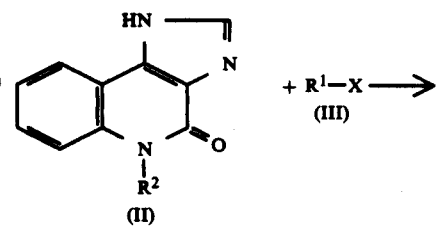

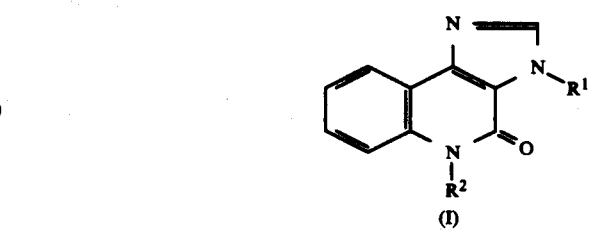

wherein $R^1$ and $R^2$ have the same significance as defined above, and X represents a leaving group.

The leaving-group denoted by X includes, for example, halogen such as chlorine, bromine, iodine, etc.; alkylsulfonyloxy such as methanesulfonyloxy, etc. or arylsulfonyloxy such as phenylsulfonyloxy, p-tolueneauldonyloxy, etc.

The reaction is performed in a solvent, preferably in the presence of a base.

The starting Compound (II) is synthesized by the method described in Reference Example 1 or according to a manner similar thereto.

The base used herein includes, for example alkali metal carbonates such as potassium carbonate, sodium carbonate, etc.; alkali metal hydrides such as sodium hydride, etc.; alkali metal alkoxides such as sodium methoxide, sodium ethoxide, etc.

Any solvent is used so long as it is inert to the reaction. The solvent includes, for example, ethers such as tetrahydrofuran, dioxan, etc.; amide such as dimethylformamide, etc.; alcohols such as methanol, ethanol, etc.; dimethylsulfoxide, etc. The solvent is used alone or in combination.

The reaction is performed at 0° to 180° C. and completed in 30 minutes to 24 hours.

Process 2

Compound (I) is also obtained from Compound (IV), by way of Compound (V).

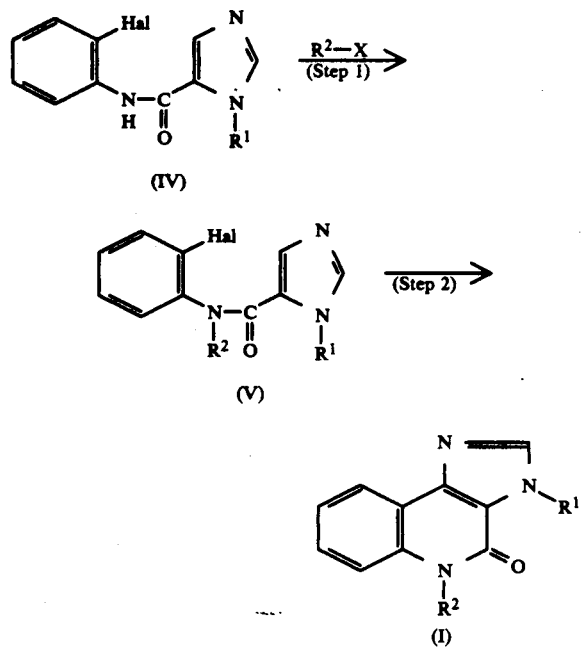

wherein $R^1$, $R^2$ and X have the same significance as defined above, and Hal represents halogen.

The halogen includes, for example, chlorine, bromine, iodine, etc.

The starting Compound (IV) is synthesized by the methods described in Reference Examples 2 and 3, and in Japanese Published Unexamined Patent Application No. 01372/78 or according to a similar manner thereto.

(Step-1)

The reaction of Compound (IV) with $R^2$-X is performed according to a manner similar to the process described in Process 1.

(Step-2A)

Compound (I) is obtained by reacting Compound (V) with a hydrogen source in a solvent in the presence of a radical initiator.

The radical initiator includes, for example, peroxides such as benzoyl peroxide, etc.; azo compounds such as azoisobutylnitrile (AIBN), etc.; trialkylborans, etc. The hydrogen source includes, for example, trialkyl tin hydrides, etc.

Any solvent is used so long as it is inert to the reaction. The solvent includes, for example, hydrocarbons such as benzene, toluene, n-hexane, etc.; halogenated hydrocarbons such as carbaon tetrachloride, etc. The solvent is used alone or in combination.

The reaction is performed at 50° to 150° C. and completed in 5 minutes to 24 hours.

(Step 2B)

Compound (I) is obtained by reacting Compound (V) with palladium. The reaction is preferably performed in the presence of a base.

The palladium includes, for example, palladium acetate, palladium chloride, tetrakistriphenylphosphine palladium, etc.

The base used herein includes, for example, alkali metal carbonates such as potassium carbonate, etc.; alkali metal hydrides such as sodium hydride, etc.; organic amines such as triethylamine, pyridine, etc.

Any solvent is used so long as it is inert to the reaction. The solvent includes, for example, ethers such as tetrahydrofuran, etc.; alcohols such as methanol, etc.; amides such as dimethylacetoamide, etc.; dimethylsulfoxide, etc. The solvent is used alone or in combination.

The reaction is performed at 0° to 200° C. and completed in 5 minutes to 24 hours.

In these processes, intermediates and desired compounds are isolated and purified by purification methods conventionally used in the organic synthetic chemistry, for example, filtration, extraction, washing, drying, concentration, recrystallization, various column chromatographies, etc. The intermediates can be immediately used in the subsequent reaction, without any particular purification.

In case that the desired Compound (I) is obtained in the form of a salts, the compound may be purified as it is. In case that Compound (I) is obtained in free form, the salts are formed in a conventional manner.

Compounds (I) and their pharmaceutically acceptable salts may exist in the form of additional products to water or various solvents, and these additional products are included in the present invention.

Representative Compounds of the present invention are shown in Table 1.

TABLE 1

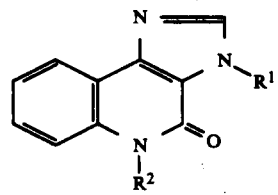

| Compound No. | Example No. | $R^1$ | $R^2$ |
|---|---|---|---|
| 1 | (1) (9) (13) | —CH₃ | —(CH₂)₃CH₃ |
| 2 | (2) | —C₂H₅ | —(CH₂)₃CH₃ |
| 3 | (3) | —(CH₂)₂CH₃ | —(CH₂)₃CH₃ |
| 4 | (4) | —CH(CH₃)₂ | —(CH₂)₃CH₃ |
| 5 | (5) | —(CH₂)₃CH₃ | —(CH₂)₃CH₃ |
| 6 | (6) | —CH₂COCH₃ | —(CH₂)₃CH₃ |
| 7 | (7) | —CH₂CO₂C(CH₃)₃ | —(CH₂)₃CH₃ |
| 8 | (8) | —CH₂CO₂H | —(CH₂)₃CH₃ |
| 9 | (10) | —CH₃ | —C₂H₅ |
| 10 | (11) | —CH₃ | —(CH₂)₂CH₃ |
| 11 | (12) | —CH₃ | —CH₂CH(CH₃)₂ |

The pharmacological activities of the Compound (I) are illustrated as follows.

(a) Effects on passive Schultz-Dale reaction (broncho-dilatory effects)

Male Hartley guinea pigs weighing 350 to 500 g were passively sensitized by intraperitoneal injection of rabbit anti-egg white albumin (EWA) serum prepared by the method of Eda et al. [Folia pharmacol., Japon 66, 237, (1970)]. After 24 hours, the guinea pigs were stunned and exsanguinated, and then tracheae were removed. The zig-zag strips of the tracheae were prepared by the method of Emmerson and Mackay [J. Pharm. Pharmacol., 31, 798, (1979)]. The strips were suspended in Krebs-Henseleit solution at 37° C. under aeration of a mixed gas of 95% oxygen and 5% carbon dioxide, and equilibrated for one hour. Antigen (EWA) was then introduced in the solution (final concentration; 1 μg/ml), and the contraction was measured by isotonic transducer (TD-112s, made by Nihon Kohden K.K., Japan) and recorded on a recorder (Type 3066, made by Yokogawa-Hokushin Denki, K.K. Japan). After the contraction curves reached plateau, the compounds were successively added in order to get cumulative concentration-relaxation curves. Concentration of 50% relaxation rate ($IC_{50}$) was calculated from the regression line, which was obtained from cumulative concentration-relaxation curves.

The results are shown in Table 2.

(b) Effects on experimental asthma

Guinea pigs were passively sensitized as follows. Male Hartley guinea pigs weighing 350 to 500g were intraperitoneally injected with 1 ml of rabbit EWA serum prepared by the method of Eda et al. [Folia pharmacol., Japon, 66, 237 (1970)]. The animals were treated with intraperitoneal injection of diphenhydramine (20 mg/kg) and propranolol (5 mg/kg), 30 minutes before administration of test compounds. 17 hours after the sensitization, the test compounds (50 mg/kg) were orally administrated to sensitized animals. After one hour from the administration of the test compounds, the guinea pigs were placed in plastic observation box and were exposed to an aerosal antigen of 1.5% EWA.

The time until the onset of respiratory distresslike symptom [collapse time (second)] was measured as a result of experimental asthma.

The results are shown in Table 2.

(c) Acute toxicity

The compounds were orally administrated (po: 300 mg/kg) to male dd-mice weighing 20 to 25 g. $LD_{50}$ was determined by observing the mortality for seven days after the administration.

The results are shown in Table 2.

TABLE 2

| Compound | Passive Schultz-Dale reaction ($IC_{50}$; μM) | Experimental asthma (Second) | Acute Toxicity ($LD_{50}$; mg/kg) |
|---|---|---|---|
| 1 | 6.7 | 429 | >200 |
| 2 | 2.0 | | >300 |
| 3 | 6.8 | 348 | >300 |
| 4 | 3.7 | | >300 |
| 5 | | | >300 |
| 6 | 7.9 | 530 | >300 |
| 7 | 0.47 | | |
| 8 | 6.7 | | |
| 9 | 1.3 | | |
| (Reference Compounds) | | | |
| Control | | 254 | |
| Aminophylline[1] | 23 | | |
| Theophylline[2] | | 414 | |

[1] The Merck Index, 11th, pp 477 (1989)
[2] The Merck Index, 11th, pp 1461 (1989)

Compounds (I) or their pharmaceutically acceptable salts are used directly or in various dosage forms. In the present invention, pharmaceutical compositions are prepared by homogeneously mixing an effective amount of Compound (I) or its pharmaceutically acceptable salt with pharmaceutically acceptable carrier. It is desirable that the pharmaceutical compositions are an appropriate dosable unit for oral administration or injection administration.

In the preparation of orally administrated forms, any of useful pharmaceutically acceptable carriers are used. In the case of orally administrated liquid preparates such as suspensions and syrups, for example, water, saccharides such as sucrose, sorbitol, fructose, etc., glycols such as polyethyleneglycol, propyleneglycol, etc., oils such as sesame oil, olive oil, soybean oil, etc., antiseptics such as p-hydroxybenzoic acid esters, etc., and flavors such as strawberry flavor, peppermint etc. are used. In the case of powder, pills, capsules and tablets; vehicles such as lactose, glucose, sucrose, mannitol, etc.; disintegrators such as starch, sodium alginate, etc.; lubricants such as magnesium stearate, talc, etc.; binders such as polyvinyl alcohol, hydroxypropyl cellulose, gelatin, etc., surfactants such as fatty acid esters etc., and plasticizers such as glycerine, etc., are used. Tablets and capsules are most useful dosage form for oral administration because of easy administration. In the preparation of tablets and capsules, solid medicament carriers are used.

Injection solutions are prepared with such a carrier as distilled water, a salt solution, a glucose solution, or a mixture of a salt solution and a glucose solution.

Effective dose and the number of administration of Compound (I) or its pharmaceutically acceptable salt depend on modes of administration and ages, body weight, and symptoms, etc. of patients. It is preferable to usually administrate 1 to 50 mg/kg of Compound (I) or its pharmaceutically acceptable salt daily in 3 to 4 portions.

Furthermore, Compound (I) is administrated by inhalation in the form of aerosol, finely pulverized powders, or spray solution. In the case of aerosol administration, Compound (I) or its pharmaceutically acceptable salt is dissolved in an appropriately pharmaceutically acceptable solvent, for example, ethyl alcohol or a combination of miscible solvents and then mixed with a pharmaceutically acceptable propellant. The aerosol composition is used by filling it in a pressure-withstanding container composition. It is preferable that the aerosol valve is a metering valve for discharging an effective dosage of aerosol composition as determined in advance.

The present invention will be described in detail below, referring to Examples and Reference Examples.

Physicochemical properties of the compounds obtained in the examples and reference examples are shown in Tables 3 and 4, respectively.

EXAMPLE 1

5-n-Butyl-3-methyl-3H,5H-imidazo[4,5,-c]quinolin-4-one (Compound 1)

1.2 g (0.0050 mol) of Compound b obtained in Reference Example 1 was suspended in 30 ml of N,N-dimethylformamide (DMF). Under ice cooling, 0.30 g (0.0075 mol) of 60% sodium hydride was added to the suspension, followed by stirring at room temperature for 30 minutes. Again under ice cooling, 0.78 ml (0.012 mol) of iodomethane was added to the reaction mixture followed by stirring at room temperature for 30 minutes. The solvent was evaporated under reduced pressure. Water was added to the residue and the mixture was extracted with chloroform. The organic layer was washed with saturated sodium chloride aqueous solution, dried over anhydrous sodium sulfate and filtered. The solvent was evaporated under reduced pressure.

The residue was purified by silica gel column chromatography (eluting solvent: chloroform /methanol=50 /1). Recrystallization from methanol-water gave 0.95 g (yield, 75%) of Compound 1.

EXAMPLE 2

5-n-Butyl-3-ethyl-3H,5H-imidazo[4,5-c]quinolin-4-one hydrochloride (Compound 2)

1.2 g (0.0050 mol) of Compound b obtained in Reference Example 1 was suspended in 30 ml of DMF. Under ice cooling, 0.30 g (0.0075 mol) of 60% sodium hydride was added to the suspension, followed by stirring at room temperature for 30 minutes. Under ice cooling, 0.96 ml (0.012 mol) of iodoethane was added to the reaction mixture followed by stirring at room temperature for 30 minutes. The solvent was evaporated under reduced pressure. Water was added to the residue and the mixture was extracted with chloroform. The organic layer was washed with saturated sodium chloride aqueous solution, dried over anhydrous sodium sulfate and filtered. The solvent was evaporated under reduced pressure.

The residue was purified by silica gel column chromatography (eluting solvent: chloroform /methanol=50 /1), and dissolved in ethyl acetate. The solution was crystallized by addition of ethyl acetate saturated with hydrochloric acid. The precipitate was collected by filtration and dried, to afford 1.1 g of Compound 2 (yield: 84%).

EXAMPLE 3

5-n-Butyl-3-n-propyl-3H,5H-imidazo[4,5-c]quinolin-4-one hydrochloride (Compound 3)

Compound 3 was obtained (yield, 80%) in a manner similar to Example 2 except that iodopropane was used instead of iodoethane.

EXAMPLE 4

5-n-Butyl-3-isopropyl-3H,5H-imidazo[4,5,-c]quinolin-4-one hydrochloride (Compound 4)

Compound 4 was obtained (yield, 68%) in a manner similar to Example 2 except that iodoisopropane was used instead of iodoethane.

EXAMPLE 5

3,5-Di-n-Butyl-3H,5H-imidazo [4,5,-c] quinolin-4-one hydrochloride (Compound 5)

Compound 5 was obtained (yield, 78%) in a manner similar to Example 2 except that iodobutane was used instead of iodoethane.

EXAMPLE 6

3-Acetonyl-5-n-butyl-3H,5H-imidazo[4,5,-c]quinolin-4-one (Compound 6)

Compound 6 was obtained (yield, 65%) in a manner similar to Example 1 except that bormoacetone was used instead of iodomethane.

EXAMPLE 7

3-tert-Butoxycarbonylmethyl-5-n-butyl-3H,5H-imidazo[4,5-c]quinolin-4-one (Compound 7)

Compound 7 was obtained (yield, 70%) in a manner similar to Example 1 except that tert-butyl bromoacetate was used instead of iodomethane.

EXAMPLE 8

5-n-Butyl-3-carboxymethyl-3H,5H-imidazo[4,5,-c]quinolin-4-one (Compound 8)

2.3 g (0.0073 mole) of Compound 7 obtained in Example 7 was dissolved in 50 ml of methylenechloride. Under ice cooling, 50 ml of trifluoro-acetic acid was added to the solution, followed by stirring at room temperature for 2.5 hours. After the solvent was evaporated, diethyl ether was added to the residue. The precipitate was washed with diethyl ether by trituration.

The obtained crystals were suspended in 40 ml of water, and pH of solution was adjusted to 5 by sodium hydroxide. The crystals were collected by filtration and dried to afford 1.5 g (yield, 77%) of Compound 8.

Recrystallization was performed from DMF-isopropyl alcohol.

EXAMPLE 9

Compound 1

After 0.66 g (2.4 mmole) of Compound d obtained in Reference Example 3 was dissolved in 15 ml of DMF, 0.12 g (3.1 mmols) of 60% sodium hydride was added to the solution under ice cooling. The mixture was stirred at room temperature for 30 minutes. Under ice cooling, 0.41 ml (3.6 mmols) of iodobutane was added to the reaction mixture followed by stirring at 50° C. for an hour. The solvent was evaporated under reduced pressure. Water was added to the residue and the mixture was extracted twice with chloroform. The organic layer was washed with saturated sodium chloride aqueous solution and dried over anhydrous sodium sulfate. After sodium sulfate was removed by filtration, the solvent was evaporated under reduced pressure.

The residue was purified by silica gel column chromatography (eluting solvent: chloroform /methanol=40 /1). 100 ml of toluene, and 16 mg (0.097 mmol) of 98% azoisobutylonitrile and 0.63 ml (2.3 mmols) of tri-n-butylhydride were added to the 0.54 g of purified product. The mixture was refluxed at 110° C. for 10 hours under a nitrogen flow.

The reaction solution was cooled to room temperature and the solvent was evaporated under reduced pressure. The obtained crude product was purified by silica gel column chromatography (eluting solvent: chloroform /methanol=50 /1) to afford 0.12 g (yield, 20%) of Compound 1.

EXAMPLE 10

5-Ethyl-3-methyl-3H,5H-imidazo[4,5,-c]quinolin-4-one (Compound 9)

1.7 g (0.0080 mol) of Compound h obtained in Reference Example 7 was suspended in 60 ml of DMF. Under ice cooling, 0.47 g (0.012 mol) of 60% sodium hydride was added to suspension. After generation of hydrogen was finished 0.99 ml (0.0016 mol) of methyl iodide was added to suspension, followed by stirring at room temperature for 1 hour. The solvent was evaporated under reduced pressure. Water was added to the residue and the mixture was extracted with chloroform. The organic layer was washed with saturated sodium chloride aqueous solution, dried over anhydrous sodium sulfate and filtered. The solvent was evaporated under reduced pressure.

The residue was purified by silica gel column chromatography (eluting solvent: chloroform /methanol=50/1), to afford 1.3 g of Compound 9 (yield, 72%).

EXAMPLE 11

3-Methyl-5-n-propyl-3H,5H-imidazo[4,5-c]quinolin-4-one (Compound 10)

Compound 10 was obtained (yield, 61%) in a manner similar to Example 10 except that Compound i obtained in Reference Example 8 was used instead of Compound h.

EXAMPLE 12

5-Isobutyl-3-methyl-3H,5H-imidazo[4,5-c]quinolin-4-one (Compound 11)

Compound 11 was obtained (yield, 95%) in a manner similar to Example 10 except that Compound j obtained in Reference Example 9 was used instead of Compound h.

EXAMPLE 13

Compound 1

100 mg (0.30 mmol) of Compound k obtained in Reference Example 10, 20 mg (0.089 mmol) of palladium acetate, and 41 mg (0.39 mmol) of sodium carbonate were suspended in 2 ml of N,N-dimethylacetoamide, and the suspension was stirred for 4 hours at 170° C. After cooling the reaction mixture, the solvent was evaporated under reduced pressure. Water was added to the residue and the mixture was extracted with chloroform. The organic layer was washed with saturated sodium chloride aqueous solution, dried over anhydrous sodium sulfate and filtered. The solvent was evaporated under reduced pressure.

Purification of the residue by thin layer chromatography (developer: chloroform /methanol=10/1) gave 46 mg (yield, 60%) of Compound 1.

TABLE 3

| Compound No. | Melting point (°C.) (Recrystallization solvent) | NMR (Measuring solvent) δ (ppm) | IR (KBr) cm$^{-1}$ | MS (m/z) | Elemental analysis (%) (upper: found lower: calculated) |
|---|---|---|---|---|---|
| 1 | 151–153 (methanol-water) | (DMSO-d$_6$) 0.95(t,3H,J=7Hz), 1.36–1.52 (m,2H), 1.58–1.71 (m, 2H), 4.08(s,3H), 4.31(t,2H, J=7Hz), 7.32(t,1H,J=9Hz), 7.43 (d,1H,J=9Hz), 7.56(t,1H,J= 9Hz), 8.17(d,1H,J=9Hz), 8.20 (s,1H) | 1660 | 255 (M$^+$) | $C_{15}H_{17}N_3O$<br>C   H   N<br>71.05  7.0  16.54<br>70.56  6.41  16.46 |
| 2 | 215–218 | (DMSO-d$_6$) 0.95(t,3H,J=7Hz), 1.35–1.54(m,2H), 1.50(t,3H, J=7Hz), 1.58–1.72(m,2H), 4.36 (t,2H,J=7Hz), 4.57(q,2H,J= 7Hz), 7.42(t,1H,J=9Hz), 7.61–7.74(m,2H), 8.35(d,1H,J=9Hz), 9.01(s,1H) | 1684 | 270 (M$^+$) | $C_{16}H_{19}N_3O \cdot HCl$<br>C   H   N<br>62.84  6.80  13.64<br>62.84  6.59  13.74 |
| 3 | 211–214.5 | (DMSO-d$_6$) 0.90(t,3H,J=7Hz), 0.95(t,3H,J=7Hz), 1.34–1.52 (m,2H), 1.57–1.71(m,2H), 1.81–1.94(m,2H), 4.35(t,2H,J=7Hz), 4.54(t,2H,J=7Hz), 7.42(t,1H, J=9Hz), 7.62–7.77(m,2H), 8.39 (d,J=9Hz), 9.14(s,1H) | 1673 | 284 (M$^+$) | $C_{17}H_{21}N_3O \cdot HCl$<br>C   H   N<br>63.83  7.13  13.17<br>63.84  6.93  13.14 |
| 4 | 203.5–205.0 | (DMSO-d$_6$) 0.96(t,3H,J=7Hz), 1.60(d,6H,J=7Hz), 1.34–1.73 (m,4H), 4.37(t,2H,J=7Hz), 5.42–5.55(m,1H), 7.43(t,1H, J=9Hz), 7.62–7.77(m,2H), 8.43 (d,1H,J=9Hz), 9.33(s,1H) | 1673 | 284 (M$^+$) | $C_{17}H_{21}N_3O \cdot 0.4HCl$<br>$\cdot 1.6H_2O$<br>C   H   N<br>62.45  7.22  12.85<br>62.42  7.58  12.86 |
| 5 | 197–203 | (DMSO-d$_6$) 0.92(t,3H,J=7Hz), 0.95(t,3H,J=7Hz), 1.23–1.51 (m,4H), 1.54–1.71(m,2H), 1.80–1.94(m,2H), 4.36(t,2H,J=7Hz), 4.57(t,2H,J=7Hz), 7.43(t,1H, J=9Hz), 7.63–7.78(m,2H), 8.40 (d,1H,J=9Hz), 9.16(s,1H) | 1668 | 297 (M$^+$) | $C_{18}H_{23}N_3O \cdot HCl$<br>C   H   N<br>64.89  7.47  12.70<br>64.76  7.25  12.59 |
| 6 | 140–142 (methanol-water) | (DMSO-d$_6$) 0.93(t,3H,J=7Hz), 1.32–1.48(m,2H), 1.53–1.68 (m,2H), 2.26(s,3H), 4.28(t, 2H,J=7Hz), 5.45(s,2H), 7.35 (t,1H,J=9Hz), 7.52–7.65(m, 2H), 8.16(s,1H), 8.20(d,1H, J=9Hz) | 1720 1648 | 297 (M$^+$) | $C_{17}H_{19}N_3O_2$<br>C   H   N<br>68.81  6.73  13.96<br>68.67  6.44  14.13 |
| 7 | — | (CDCl$_3$) 1.00(t,3H,J=7Hz), 1.48(s,9H), 1.20–1.93(m,4H), 4.35(t,2H,J=7Hz), 5.23(s,2H), 7.18–7.50(m,2H), 7.876(s,1H), 8.32(d,1H,J=9Hz) | — | 353 (M$^+$) | — |
| 8 | 225–227 (DMF-iso-propyl alcohol) | (DMSO-d$_6$) 0.93(t,3H,J=7Hz), 1.32–1.50(m,2H), 1.52–1.68 (m,2H), 4.30(t,2H,J=7Hz), 5.29 (s,2H), 7.36(t,1H,J=9Hz), 7.54–7.65(m,2H), 8.20(d,1H,J=9Hz), 8.31(s,1H), 12.85–13.40(brs, 1H) | 3600–2200 1725 1657 | 299 (M$^+$) | — |

TABLE 3-continued

| Compound No. | Melting point (°C.) (Recrystallization solvent) | NMR (Measuring solvent) δ (ppm) | IR (KBr) cm⁻¹ | MS (m/z) | Elemental analysis (%) (upper: found lower: calculated) |
|---|---|---|---|---|---|
| 9 | 137–140 (diisopropyl ether) | (DMSO-d₆) 8.21(s,1H), 8.17 (d,1H,J=8Hz), 7.09–7.66(m,3H), 4.38(q,2H,J=7Hz), 4.08(s,3H), 1.26(t,3H,J=7Hz) | 1652 1515 | — | C₁₃H₁₃N₃O<br>C   H   N<br>68.70  5.93  18.65<br>68.71  5.77  18.49 |
| 10 | 124–126 (diisopropyl ether) | (DMSO-d₆) 8.21(s,1H), 8.17(d, 1H,J=8Hz), 7.15–7.65(m,3H), 4.28(t,2H,J=7Hz), 4.07(s,3H), 1.40–1.85(m,2H), 0.97(t,3H, J=7Hz) | 1659 1574 | — | C₁₄H₁₅N₃O<br>C   H   N<br>69.57  6.44  17.42<br>69.69  6.27  17.41 |
| 11 | 137–140 (diisopropyl ether) | (DMSO-d₆) 8.22(s,1H), 8.12(d, 1H,J=8Hz), 7.20–7.69(m,3H), 4.22(d,2H,J=7Hz), 4.07(s,3H), 1.97–2.30(m,1H), 0.92(d,6H, J=7Hz) | 1659 1652 | — | C₁₅H₁₇N₃O<br>C   H   N<br>70.40  6.90  16.62<br>70.56  6.71  16.64 |

REFERENCE EXAMPLE 1

5-n-Butyl-1H,5H-imidazo[4,5-c]quinolin-4-one (Compound b)

After 4.1 g (0.015 mol) of 1-benzyl-4-hydroxy1H-imidazo[4,5-c]quinoline was suspended in 50 ml of DMF, 0.80 g (0.020 mol) of 60% sodium hydride was added to the suspension under ice cooling. The mixture was stirred at room temperature for 30 minutes. Under ice cooling, 2.6 ml (0.023 mol) of iodobutane was added to the reaction mixture followed by stirring at 50° C. for 2 hours. The solvent was evaporated under reduced pressure. Water was added to the residue and the mixture was extracted with chloroform. The organic layer was washed with saturated sodium chloride aqueous solution, and dried over anhydrous sodium sulfate. After anhydrous sodium sulfate was removed by filtration, the solvent was evaporated under reduced pressure. The obtained crude product was purified by silica gel column chromatography (eluting solvent: chloroform /methanol=17 /1). Recrystallization from iso-propanol-isopropyl ether gave 2.5 g (yield, 65%) of 1-benzyl-5-n-butyl-1H,5H-imidazo[4,5-c]quinolin-4-one (Compound a).

After 2.4 g (0.071 mol) of the Compound a was dissolved in 115 ml of acetic acid, 0.48 g of 10% palladium/carbon was added to the solution. The mixture was stirred at 70° C. for 4 hours under a hydrogen flow. The reaction solution was filtered and the filtrate was concentrated under reduced pressure. The concentrate was neutralized with saturated sodium hydrogencarbonate aqueous solution and the precipitate was taken by filtration. The precipitate was recrystallized from ethanol-water to afford 1.5 g (yield, 86%) of Compound b.

REFERENCE EXAMPLE 2

N-(2-Bromo)phenyl-1H-imidazol-5-carboxamide (Compound c)

After 21.7 ml (0.20 mol) of 2-bromoaniline was dissolved in 200 ml of DMF, 8.1 g (0.20 mol) of 60% sodium hydride was added to the solution under ice cooling. After generation of hydrogen was finished, 9.5 g (0.051 mol) of diimidazo[3,4-d:3',4'-d]piperazine-2,5-dione [J. Chem. Soc., Part D: Chem. Comm., 162, (1975)]was added to the reaction mixture. The mixture was stirred at room temperature for 2 hours. After conclusion of the reaction, the solvent was evaporated under reduced pressure. Water and chloroform were added to the residue and the mixture was stirred for 30 minutes to obtain a reaction product. The filtration and drying of the product were performed, to afford 5.7 g (yield, 42%) of Compound c.

REFERENCE EXAMPLE 3

N-(2-Bromo)phenyl-1-methylimidazol-5-carboxamide (Compound d)

After 2.6 g (0.010 mol) of Compound c obtained in Reference Example 2 was added to 0.88 g (0.013 mol) of potassium hydroxide in 15 ml of ethanol at room temperature, the mixture was allowed to stand for 30 minutes to one hour, and 3.0 ml (0.021 mol) of iodomethane was added to the mixture under ice cooling.

After the mixture was allowed to stand overnight, 100 ml of water was added and the reaction solution was filtered to obtain a reaction product. The product was taken out by filtration and dissolved in chloroform. After chloroform layer was washed with water, 1 N sodium hydroxide aqueous solution and saturated sodium chloride aqueous solution in order, the solution was dried over anhydrous sodium sulfate. After filtration, the solvent was evaporated under reduced pressure to afford 2.0 g (yield, 72%) of Compound d.

REFERENCE EXAMPLE 4

1-Benzyl-5-ethyl-1H,5H-imidazo[4,5-c]quinolin-4-one (Compound e)

4.0 g (0.015 mol) of 1-Benzyl-4-hydroxy-1H-imidazo[4,5-c]quinolin was suspended in 100 ml of N,N-dimethylformamide. Under ice cooling, 0.87 g (0.022 mol) of sodium hydroxide was added to the suspension. After generation of hydrogen was finished, 2.3 ml (0.029 mol) of ethyl iodide was added to the suspension, and the mixture was stirred at room temperature for 1.5 hours. The reaction mixture was evaporated under reduced pressure. Water was added to the residue and the mixture was extracted with chloroform. Extracted organic layer was washed with saturated sodium chloride aqueous solution, and dried over anhydrous sodium sulfate. After anhydrous sodium sulfate was removed by filtration, the filtrate was evaporated under reduced pressure.

The obtained crude product was purified by silica gel column chromatography (eluting solvent: chloroform /methanol=50 /1). Recrystallization from ethanol-water gave 2.7 g (yield, 62%) of Compound e.

REFERENCE EXAMPLE 5

1-Benzyl-5-n-propyl-1H,5H-imidazo[4,5,-c]quinolin-4-one (Compound f)

Compound f was obtained (yield, 70%) in a manner similar to Reference Example 4 except that n-propyl iodide was used instead of ethyl iodide.

REFERENCE EXAMPLE 6

1-Benzyl-isobutyl-1H,5H-imidazo[4,5,-c]quinolin-4-one (Compound g)

Compound g was obtained (yield, 60%) in a manner similar to Reference Example 4 except that isobutyl iodide was used instead of ethyl iodide.

REFERENCE EXAMPLE 7

5-Ethyl-1H,5H-imidazo[4,5-c]quinolin-4-one (Compound h)

3.0 g (0.0099 mol) of Compound e obtained in Reference Example 4 was dissolved in 110 ml of acetic acid. 0.89 g of 10% palladium carbon was added to the solution. Under hydrogen stream, the solution was stirred 3 hours at 70° C. After filtration, the filtrate was concentrated under reduced pressure. Anhydrous sodium carbonate was added to the solution for neutralization, and a precipitate was collected by filtration and recrystallized from isopropanol-water, to afford 2.0 g (yield: 93%) of Compound h.

REFERENCE EXAMPLE 8

5-n-Propyl-1H,5H-imidazo[4,5-c]quinolin-4-one (Compound i)

Compound i (yield, 94%) was obtained in a similar manner to Reference Example 7 except that Compound f obtained in Reference example 5 was used instead of Compound e.

REFERENCE EXAMPLE 9

5-Isobutyl-1H,5H-imidazo[4,5-c]quinolin-4-one (Compound j)

Compound j (yield, 94%) was obtained in a similar manner to Reference Example 7 except that Compound g obtained in Reference Example 6 was used instead of Compound e.

REFERENCE EXAMPLE 10

N-(2-Bromo)phenyl-N'-butyl-1-methylimidazol-5-carboxamide (Compound k)

0.48 g (1.8 mmol) of Compound d obtained in Reference Example 3 and 0.47 g (7.2 mmol) of 86% potassium hydroxide were suspended in 10 ml of acetone. After addition of 0.41 ml (3.6 mmol) of iodobutane, the solution was refluxed under heating. After cooling, the solvent was evaporated under reduced pressure, and water was added to the residue and the mixture was extracted with chloroform. The organic layer was washed with saturated sodium chloride aqueous solution, dried over anhydrous sodium sulfate and filtered. The residue was purified by silica gel column chromatography (eluting solvent: chloroform /methanol=50 /1) to afford 0.53 g (yield, 88%) of Compound k.

TABLE 4

| Compound No. | Melting point (°C.) (Recrystallization solvent) | NMR (Measuring solvent) δ (ppm) | IR (KBr) cm$^{-1}$ | MS (m/z) | Elemental analysis (%) (upper: found lower: calculated) |
| --- | --- | --- | --- | --- | --- |
| b | 269–271 (ethanol-water) | (DMSO-d$_6$) 0.95(t,3H,J=7Hz), 1.33–1.51(m,2H), 1.57–1.73(m, 2H), 4.36(t,2H,J=7Hz), 7.34 (t,1H,J=9Hz), 7.55(t,1H,J=9Hz), 7.62(d,1H,J=9Hz), 8.23 (s,1H), 13.40–13.70(brs,1H) | 3104, 1651, 1520, 1036, 691 | — | C$_{14}$H$_{15}$N$_3$O<br>C   H   N<br>69.86  6.30  17.29<br>69.69  6.27  17.41 |
| c | 182–187 (ethanol-water) | (CDCl$_3$ + d-MeOH) 7.00(dt,1H, J$_1$=1Hz, J$_2$=8Hz), 7.33(dt,1H, J$_1$=1Hz, J$_2$=8Hz), 7.45–7.82(m, 3H), 8.40(dd,1H,J$_1$=1Hz, J$_2$=8Hz) | 1665 | 265, 267 (M$^+$) | — |
| d | 147–149.5 (ethanol) | (DMSO-d$_6$) 3.74(s,3H), 7.02(dt, 1H,J$_1$=1Hz, J$_2$=8Hz), 7.37(dt, 1H,J$_1$=1Hz, J$_2$=8Hz), 7.64(dd, 1H,J$_1$=1Hz, J$_2$=8Hz), 7.79(d, 1H,J=1Hz), 7.88(d,1H,J=1Hz), 8.38(dd,1H,J$_1$=1Hz, J$_2$=8Hz), 9.60(brs,1H) | 1674 | 279, 281 (M$^+$) | — |
| e | 168–170 (ethanol-water) | (CDCl$_3$) 1.39(t,3H,J=7Hz), 4.49 (q,2H,J=7Hz), 5.69(s,2H), 6.91--7.52(m,8H), 7.70(d,1H,J=8Hz), 7.81(s,1H) | 1651 1568 | — | C$_{19}$H$_{17}$N$_3$O<br>C   H   N<br>75.02  5.55  13.97<br>75.22  5.64  13.85 |
| f | 269–273 (ethanol-water) | (CDCl$_3$) 1.06(d,3H,J=7Hz), 1.62–2.03(m,2H), 4.40(t,2H,J=7Hz), 5.69(s,2H), 6.97–7.52(m,8H), 7.71(d,1H,J=8Hz), 7.82(s,1H) | 1650 1572 | — | C$_{20}$H$_{19}$N$_3$O<br>C   H   N<br>75.60  5.84  13.17<br>75.68  6.03  13.23 |
| g | — | (CDCl$_3$) 1.01(d,6H,J=7Hz), 1.99–2.45(m,1H), 4.32(d,2H,J=7Hz), 5.69(s,2H), 6.83–7.52(m,8H), 7.70(d,1H,J=8Hz), 7.81(s,1H) | — | — | C$_{21}$H$_{21}$N$_3$O<br>C   H   N<br>75.89  6.51  12.62<br>76.11  6.37  12.68 |
| h | >300 (isopropanol) | (DMSO-d$_6$) 1.27(t,3H,J=7Hz), 4.42(q,2H,J=7Hz), 7.07–7.72 (m,4H), 7.93–8.36(m,2H) | 1656 1509 | — | C$_{12}$H$_{11}$N$_3$O<br>C   H   N<br>67.62  5.44  19.67<br>67.59  5.20  19.71 |

TABLE 4-continued

| Compound No. | Melting point (°C.) (Recrystallization solvent) | NMR (Measuring solvent) δ (ppm) | IR (KBr) cm⁻¹ | MS (m/z) | Elemental analysis (%) (upper: found lower: calculated) |
|---|---|---|---|---|---|
| i | >300 (ethanol-water) | (DMSO-d₆) 0.97(t,3H,J=7Hz), 1.45–1.99(m,2H), 4.30(t,2H, J=7Hz), 7.14–7.90(m,4H), 7.90–8.32(m,2H) | 1650 1575 | — | C₁₃H₁₃N₃O<br>C   H    N<br>68.65 5.75 18.56<br>68.71 5.77 18.49 |
| j | 296–300 | (DMSO-d₆) 0.92(d,6H,J=7Hz), 1.95–2.36(m,1H), 4.27(d,2H, J=7Hz), 7.02–7.75(m,4H), 7.95–8.45(m,2H) | 1663 1568 | — | C₁₄H₁₅N₃O<br>C   H    N<br>69.32 6.34 17.36<br>69.69 6.27 17.41 |
| k | — | (CDCl₃) 7.61(d,1H,J=8Hz), 6.70–7.50(m,4H), 3.20–3.80 and 4.02–4.45(m,2H), 3.55(s,3H), 1.17–1.85(m,4H), 0.95(t,3H, J=7Hz) | — | — | — |

Pharmaceutical Preparation 1

Tablet

A tablet having the following composition is prepared in a conventional manner.

| Compound 1 | 50 mg |
|---|---|
| Lactose | 113 mg |
| Potato starch | 30 mg |
| Hydroxypropylcellulose | 6 mg |
| Magnesium stearate | 0.6 mg |

Pharmaceutical Preparation 2

Powder

Powders having the following composition are prepared in a conventional manner.

| Compound 1 | 50 mg |
|---|---|
| Lactose | 750 mg |

Pharmaceutical Preparation 3

Syrup

Syrup having the following composition is prepared in a conventional manner.

| Compound 1 | 50 mg |
|---|---|
| Refined sugar | 75 mg |
| Ethyl p-hydroxybenzoate | 100 mg |
| Propyl p-hydroxybenzoate | 25 mg |
| Strawberry flavor | 0.25 cc |

Water is added to make the whole volume 100 cc.

Pharmaceutical Preparation 4

Capsule

Capsule having the following composition is prepared in a conventional manner.

| Compound 1 | 50 mg |
|---|---|
| Avicel | 69.5 mg |
| Magnesium stearate | 0.5 mg |

The composition was mixed and packed in a gelatin capsule.

Pharmaceutical Preparation 5

Injection

Injection having the following composition is prepared in a conventional manner.

| Compound 1 | 10 mg |
|---|---|
| Buffer agent | proper quantity |

Water for injection was added to the composition to make the whole volume 1.0 ml (amount per 1 ampoule). The solution was distilled and sterilized in an autoclave.

What is claimed is:

1. An imidazoquinolone compound represented by the formula

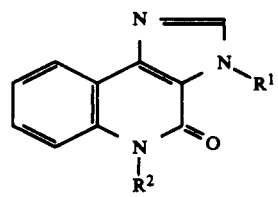

wherein $R^1$ represents lower alkyl or $-(CH_2)_mCO-R^3$ where $R^3$ represents hydrogen, lower alkyl, hydroxy or lower alkoxy; and m is an integer of 1 to 3; $R^2$ represents lower alkyl; or a pharmaceutically acceptable salt thereof.

2. A compound according to claim 1, which is selected from the group consisting of 5-n-butyl-3-methyl-3H,5H-imidazo[4,5-c]quinolin-4-one, 5-n-butyl-3-ethyl-3H,5H-imidazo[4,5-c]quinolin-4-one, 5-n-butyl-3-n-propyl-3H,5H-imidazo[4,5-c]quinolin-4-one, 5-n-butyl-3-isopropyl-3H,5H-imidazo[4,5-c]quinolin-4-one, 3,5-di-n-butyl-3H,5H-imidazo[4,5-c]quinolin-4-one, 3-acetonyl-5-n-butyl-3H,5H-imidazo[4,5-c]quinolin-4-one, 3-tert-butoxycarbonylmethyl-5-n-butyl-3H,5H-imidazo[4,5-c]quinolin-4-one, 5-n-butyl-3-carboxymethyl-3H,5H-imidazo[4,5-c]quinolin-4-one, 5-ethyl-3-methyl-3H,5H-imidazo[4,5-c]quinolin-4-one, 3-methyl-5-n-propyl-3H,5H-imidazo[4,5-c]quinolin-4-one and 5-isobutyl-3-methyl-3H,5H-imidazo[4,5-c]quinolin-4-one.

3. A compound according to claim 1, wherein said salt is selected from the group consisting of acid addition salt, metal salt, ammonium salt, inorganic amine addition salt and amino acid addition salt.

4. A pharmaceutical composition comprising a pharmaceutical carrier and, as an active ingredient, an effective amount of the compound as defined by claim 1.

* * * * *

UNITED STATES PATENT AND TRADEMARK OFFICE
CERTIFICATE OF CORRECTION

PATENT NO. : 5,010,084
DATED : April 23, 1991
INVENTOR(S) : FUMIO SUZUKI, ET AL.

It is certified that error appears in the above-identified patent and that said Letters Patent is hereby corrected as shown below:

COLUMN 2

Line 52, "tolueneauldonyloxy, should read --toluenesulfonyloxy,--.

COLUMN 3

Line 40, "No. 01372/78" should read --No. 101372/78--.

COLUMN 5

TABLE 2, "(Reference Compounds)       254
          Control"

should read --(Reference Compounds)
               Control                254--.

COLUMN 11

Line 24, "1-benzyl-4-hydroxy1H-" should read --1-benzyl-4-hydroxy-1H--.

Signed and Sealed this

Tenth Day of November, 1992

Attest:

DOUGLAS B. COMER

Attesting Officer          Acting Commissioner of Patents and Trademarks